US011129601B1

(12) United States Patent
Huber

(10) Patent No.: US 11,129,601 B1
(45) Date of Patent: Sep. 28, 2021

(54) ENDOSCOPIC SUCTION BIOPSY CATHETER WITH NO MOVING PARTS

(71) Applicant: Thomas Paul Huber, Lake Oswego, OR (US)

(72) Inventor: Thomas Paul Huber, Lake Oswego, OR (US)

(*) Notice: Subject to any disclaimer, the term of this patent is extended or adjusted under 35 U.S.C. 154(b) by 0 days.

(21) Appl. No.: 16/793,511

(22) Filed: Apr. 29, 2020

(51) Int. Cl.
*A61B 10/02* (2006.01)
*A61B 10/04* (2006.01)
*A61B 1/018* (2006.01)
*A61B 17/32* (2006.01)
*A61B 1/015* (2006.01)
*A61B 17/00* (2006.01)

(52) U.S. Cl.
CPC .......... *A61B 10/0283* (2013.01); *A61B 1/015* (2013.01); *A61B 1/018* (2013.01); *A61B 10/0266* (2013.01); *A61B 10/04* (2013.01); *A61B 17/320016* (2013.01); *A61B 2010/0225* (2013.01); *A61B 2017/0034* (2013.01); *A61B 2017/00526* (2013.01); *A61B 2217/005* (2013.01)

(58) Field of Classification Search
None
See application file for complete search history.

(56) References Cited

U.S. PATENT DOCUMENTS

| 5,013,300 | A | * | 5/1991 | Williams | A61M 1/008 433/91 |
| 5,527,332 | A | * | 6/1996 | Clement | A61B 17/320016 604/35 |
| 5,873,886 | A | * | 2/1999 | Larsen | A61B 10/04 606/159 |
| 6,478,805 | B1 | * | 11/2002 | Marino | A61B 17/1604 606/170 |
| 8,882,680 | B2 | | 11/2014 | Furlong et al. | |
| 10,231,715 | B2 | | 3/2019 | Quick et al. | |
| 2005/0187537 | A1 | * | 8/2005 | Loeb | A61B 17/32002 606/1 |
| 2008/0195066 | A1 | * | 8/2008 | Speeg | A61B 10/0275 604/326 |
| 2009/0287114 | A1 | * | 11/2009 | Lee | A61B 10/0266 600/566 |
| 2012/0165832 | A1 | * | 6/2012 | Oostman, Jr. | A61F 2/10 606/131 |
| 2018/0014819 | A1 | * | 1/2018 | Fischer | A61B 10/0283 |
| 2020/0085415 | A1 | * | 3/2020 | Dearden | A61B 10/0275 |

* cited by examiner

*Primary Examiner* — Matthew Kremer
(74) *Attorney, Agent, or Firm* — Lowenstein Sandler LLP

(57) ABSTRACT

An endoscopic biopsy device is configured to collect multiple samples from a body without removal of the device from the body. The device includes; an elongate tube of having a distal end, a proximal end, and a lumen extending from the distal end to the proximal end. The device includes a cutting element disposed in an opening of the distal end, the cutting member being immovable relative to the elongate tube and comprising a cutting surface that faces into the elongate tube and away from the distal end of the elongate tube and a blunting surface that faces outward from the elongate tube. The device further includes a valve disposed proximate to the proximal end.

18 Claims, 8 Drawing Sheets

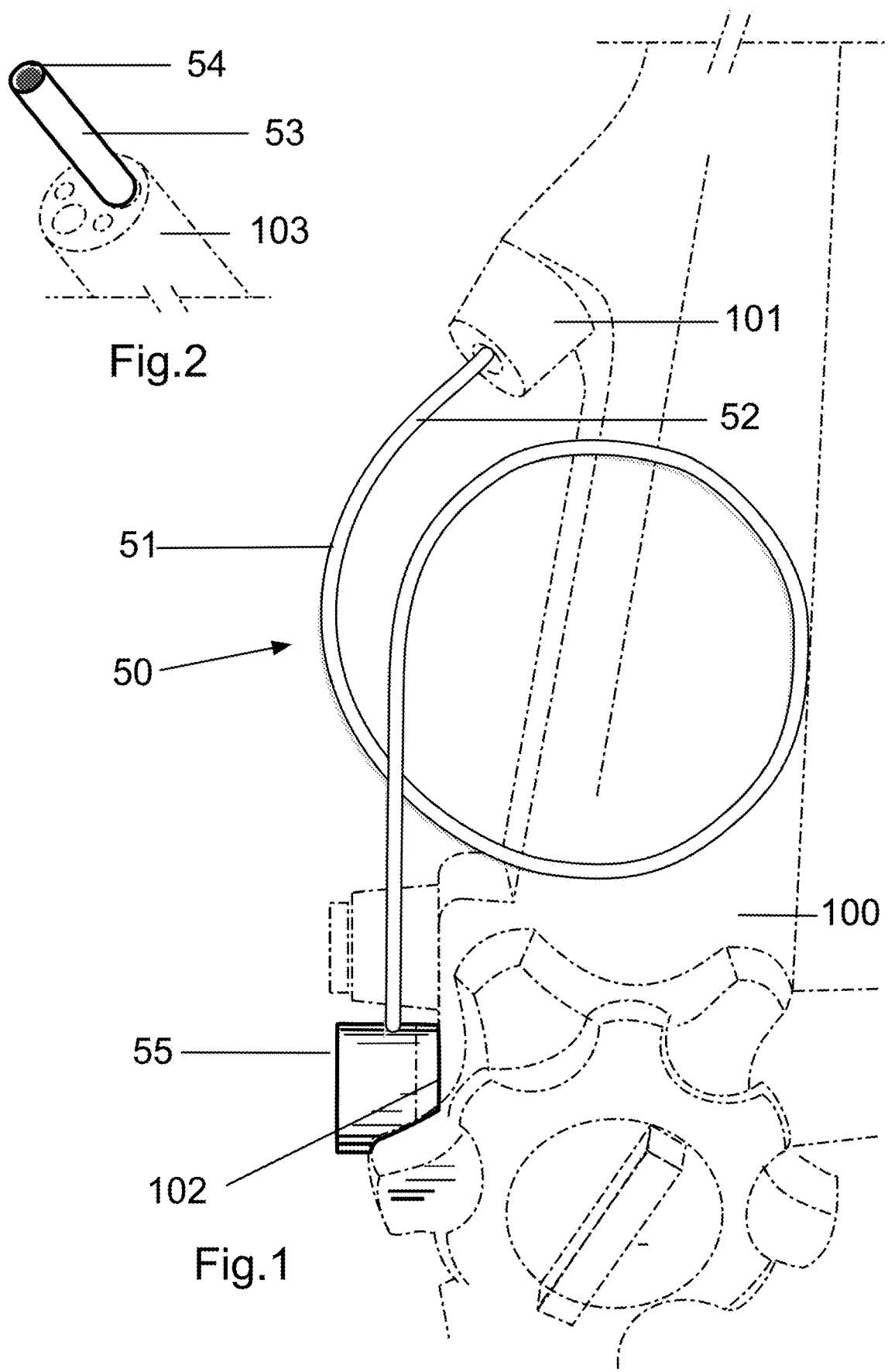

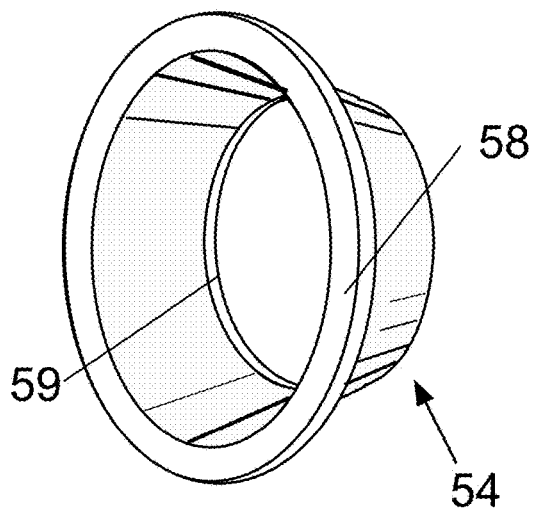 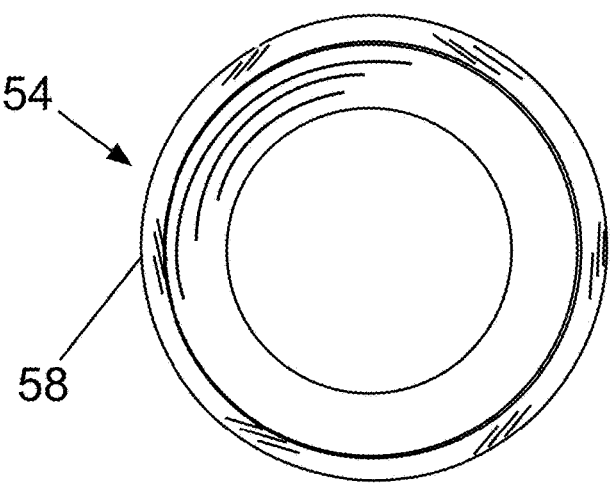
Fig.3   Fig.3A
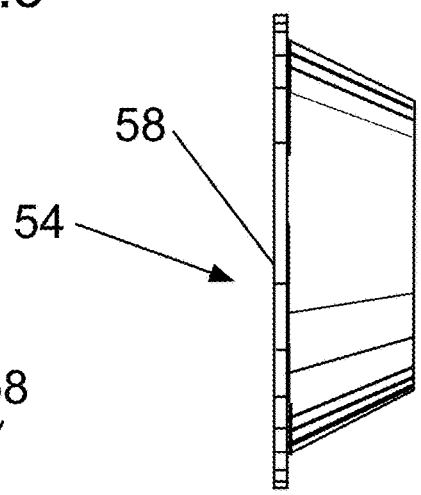
Fig.3B
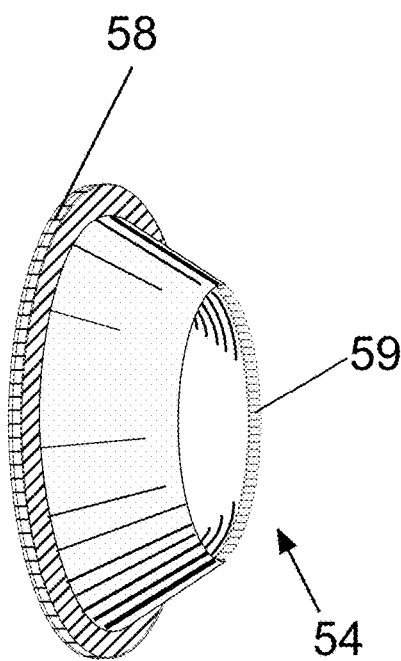 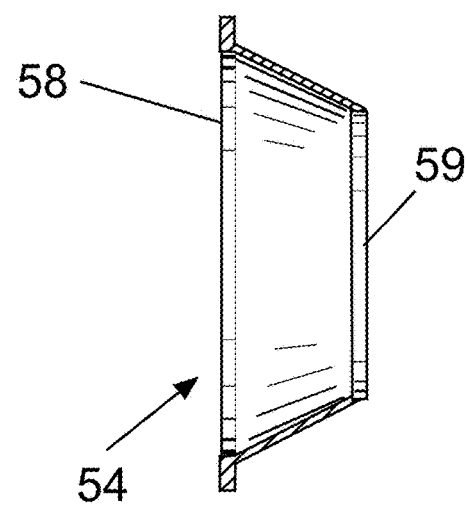
Fig.3C   Fig.3D

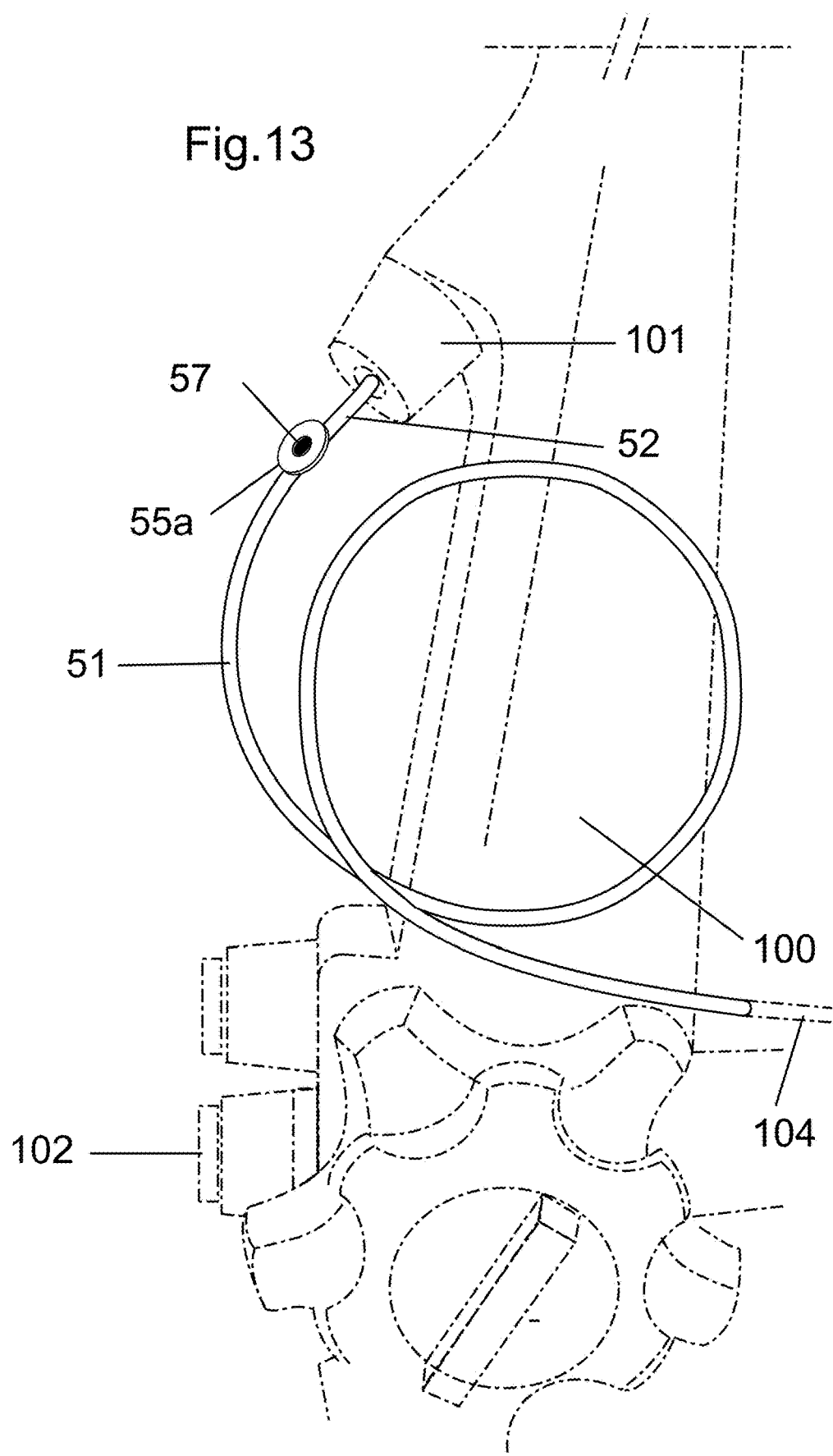

ENDOSCOPIC SUCTION BIOPSY CATHETER WITH NO MOVING PARTS

TECHNICAL FIELD

The embodiment relates generally to medical biopsy devices. More particularly, the embodiment pertains to devices for endoscopic biopsy.

BACKGROUND

The following is a tabulation of some prior art that presently appears relevant:

| Patent Number | Kind Code | Issue Date | Patentee |
|---|---|---|---|
| 8882680 | B2 | Nov. 11, 2014 | Furlong |
| 10231715 | B2 | Mar. 19, 2019 | Quick |

Endoscopy is often performed to obtain tissue samples to aid in the diagnosis of, screening for, and monitoring of, disease conditions. The structure of the luminal surface of viscera is composed of a mucosal surface layer composed of glandular cells, and beneath it, a submucosal layer composed of weak connective tissue. This tissue plane allows mucosal samples to be separated from the submucosa with little force and distortion.

Mucosal samples are collected to determine the distribution, location, and severity of disease activity by microscopic examination. It is important that the samples be collected intact and of sufficient size, to preserve microscopic structural detail. It is also important to segregate collected samples in order to preserve information as to the location from which the samples were removed.

Presently, samples are retrieved by withdrawal of the entire biopsy device from the endoscope and the samples then transferred to separate individually labelled receptacles for transport for preparation for microscopic examination. This biopsy process is limited to a small number of samples per repetition. Where multiple biopsies are taken from multiple sites, this can be a time-consuming process. In some cases, forty or more samples are required. Commonly used biopsy forceps allow two samples to be taken per repetition, thus requiring twenty passes of the forceps. Each repetition takes one minute. This adds twenty minutes to the procedure and sedation time, increasing costs and risk.

Existing biopsy devices utilize movable cutting surfaces, such as opposing surfaces or a rotating cutting surface, requiring an actuating mechanism, which complicates construction and increases risk of failure with repeated use. U.S. Pat. No. 8,882,680 (2014) uses a complex rotary system to debride a polyp and return the sample though suction. It does not, however, preserve the histologic architecture of the sample, instead reducing it to "cytological sawdust". U.S. patent Ser. No. 10/231,715 (2019) uses a rotatable blade inserted into the tissue. Vacuum is mentioned as a means of transporting samples externally, but is not an integral feature of its function.

SUMMARY OF THE INVENTION

An embodiment of an endoscopic biopsy device for collection multiple samples without removal of the device, wherein the device comprises
- an elongate tube having in an axial direction a distal end and a proximal end;
  - a cutting element affixed within the distal end and;
  - a suction valve affixed to the proximal end.

The tube is of sufficient diameter, length, composition, and flexibility to be introduced into and through an instrument channel of an endoscope, and protrude from a distal end of the endoscope. The tube has a lumen of sufficient diameter to accept the disposition of the cutting element, to allow transmission of suction from the suction valve, and to provide for passage of a specimen proximally.

The cutting element is a hollow cone having a distal base end and a proximal truncated end and is of sufficient diameter to be disposed within the lumen of the tube. The truncation may be angled, and therefore may be circular or oval. The truncated end possesses a beveled edge and may be manufactured by stamping, casting, milling, or depositing material capable of retaining a sharp edge. The proximal truncated end is disposed axially within the lumen of the distal end of the tube. The distal base of the cutting element possesses a flange of sufficient size to be affixed onto the distal end of the tube. The flange may be angled, and therefore may be circular or oval.

The valve has a conduit with a distal end that is contiguous with the lumen of the proximal end of the tube and a proximal end that may be connected to a suction source. The suction source may be that of an endoscope or a separate suction device. The conduit has a fenestration open to the ambient air.

Method for taking a tissue specimen using the device, the method comprising the steps of
  (a) inserting the distal end of the device into the instrument channel of the endoscope and slidably translating the proximal end of the device into the instrument channel until the distal end of the device appears in the visual field of the endoscope;
  (b) positioning the distal end of the device to a selected sampling site by deploying the distal portion of the tube to contact the sampling site by translating the proximal portion of the tube, by maneuvering the endoscope, or by both;
  (c) occluding the fenestration of the valve, suction causing a specimen to be drawn into the distal end of the device and traversing the proximal end of the cutting element;
  (d) Withdrawing the proximal end of the tube a short distance, causing the distal end of the tube to be translated away from the sampling site, the cutting element transecting the specimen, and the distal end of the device, no longer being in contact with the sampling site, permits suction to cause the specimen to be drawn through the lumen of the tube to an external collection device interposed between the valve and the suction source;
  (e) un-occluding the fenestration.

Method for taking subsequent specimens further comprising the steps of
  (f) selecting a further sampling site;
  (g) repeating steps (b)-(e) until the required number of specimens is collected.

Thus a large number of specimens can be collected and segregated efficiently without removing the device from the endoscope, reducing procedure and anesthesia time.

BRIEF DESCRIPTION OF THE DRAWINGS

Illustrated embodiments of the present invention are described herein with reference to the accompanying drawings, in which:

FIG. 1 is a perspective detail view of one embodiment of a proximal portion of a biopsy device positioned between the instrument channel and suction channel of an endoscope.

FIG. 2 is a perspective detail view of a distal portion of a biopsy device protruding from the instrument channel of the distal end of an endoscope.

FIG. 3 is a front perspective view of one embodiment of a cutting element.

FIG. 3A is a front orthogonal view of FIG. 3.

FIG. 3B is a left orthogonal view of FIG. 3.

FIG. 3C is a rear perspective view of FIG. 3.

FIG. 3D is a cross sectional view of FIG. 3B.

FIG. 13 is a perspective detail view of another embodiment of the proximal portion of a biopsy device positioned between the instrument channel and an external suction device (not shown).

DRAWINGS—REFERENCE NUMERALS

Figure 4:
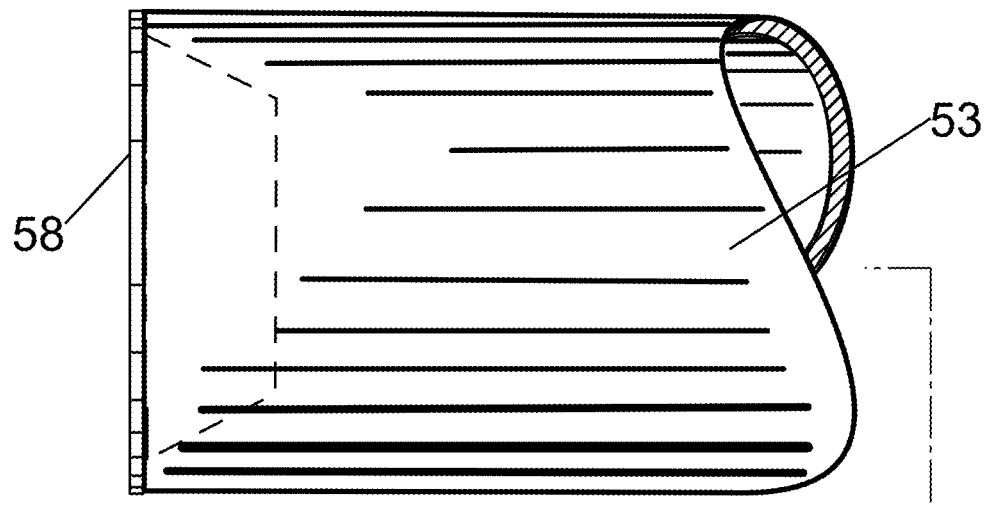
FIG. 4 is a left orthogonal view of a distal portion of a biopsy device.

50 Biopsy device
51 Tube
52 Proximal end of tube
53 Distal end of tube
54 Cutting element
55 Suction valve
55a Suction valve
56 Conduit
57 Fenestration
58 Flange
59 Beveled cutting edge
100 Handle of endoscope
101 Instrument port of endoscope
102 Suction port of endoscope
103 Distal end of endoscope
104 Suction tubing
200 Mucosal layer
201 Submucosal layer

DETAILED DESCRIPTION

It would be advantageous to provide a biopsy device of simple construction and without moveable parts that permits the resection of intact specimens and is able to transport the specimens to an external collection device without the need to remove the biopsy device from the endoscope. A large number of samples could therefore be obtained in a short period, reducing procedure time and anesthesia risk.

FIG. 1 illustrates an embodiment of a biopsy device (50) as it is to be used. The proximal end (52) of the tube (51) is situated in the instrument port (101) of an endoscope handle (100). Suction valve (55) occupies the suction port (102) of the endoscope (100). Proximal end (52) may be slidably translated to position the device (50).

FIG. 2 illustrates the distal end of the tube (53) projecting from the distal end of the endoscope (103). Cutting element (54) is disposed within the distal end of the tube (53) and may be placed in contact with a potential sampling site. Cutting element (54) may be manufactured by stamping, casting, milling, or depositing material capable of retaining a sharp edge.

FIG. 3 shows details of cutting element (54) demonstrating the position of flange (58) and cutting edge (59).

FIG. 3A shows an axial view of the distal end of cutting element (54)

FIG. 3B shows a lateral view of cutting element (54)

FIG. 3C shows detail of the cutting edge (59)

FIG. 3D shows a cross sectional view of the interior of cutting element (54)

FIG. 4 shows detail of the disposition of cutting element (54) within distal end of tube (53).

Figure 5:
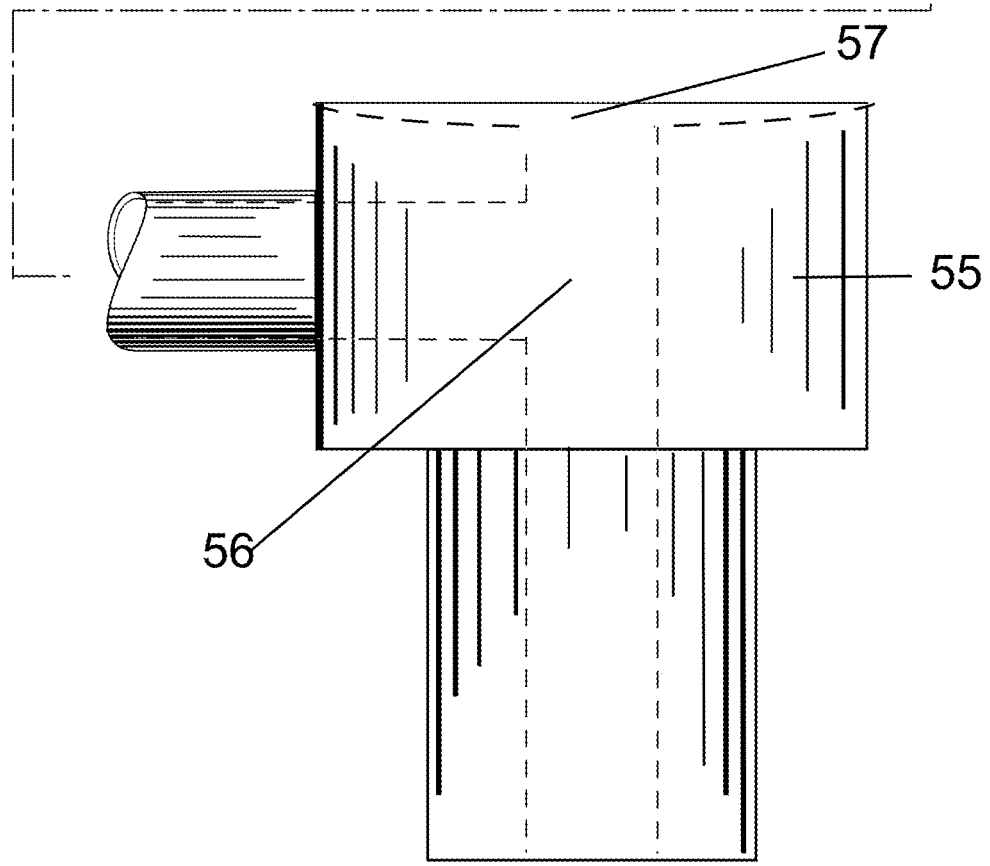
FIG. 5 is a left orthogonal view of an embodiment of a valve.

FIG. 5 shows detail of one embodiment of valve (55).

Figure 6:
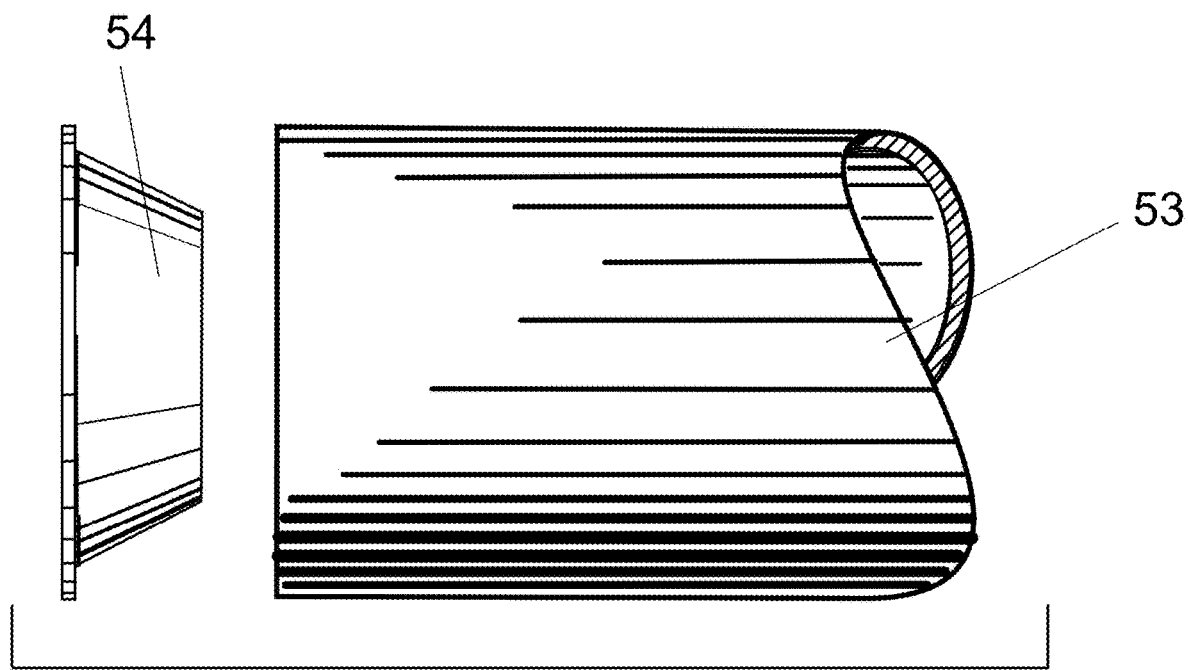
FIG. 6 is an exploded left orthogonal view of a distal portion of a biopsy device.

FIG. 6 shows an exploded view of distal end of the tube (53) showing cutting element (54) and catheter (51).

Figure 7:
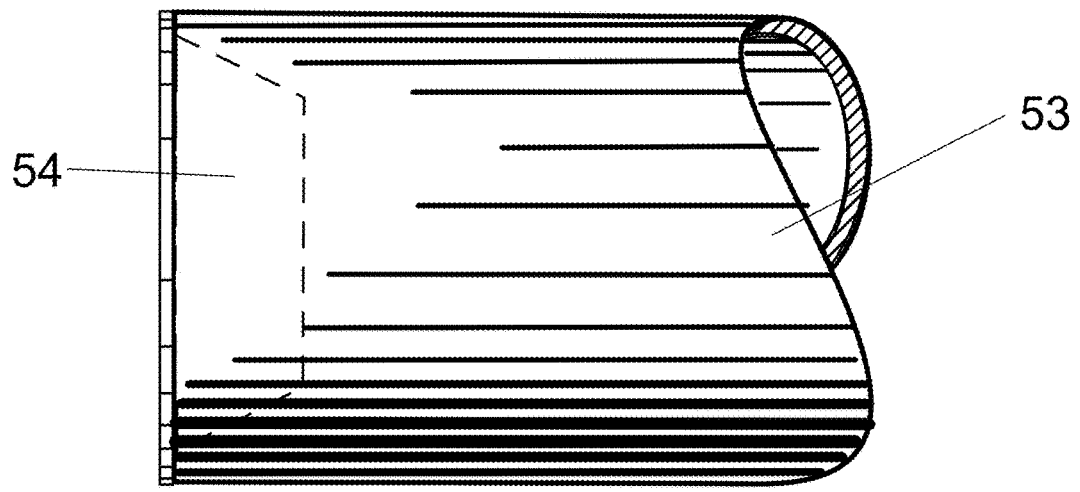
FIG. 7 is an assembled view of FIG. 6.

FIG. 7 shows the elements of FIG. 6 as assembled.

Figure 8:
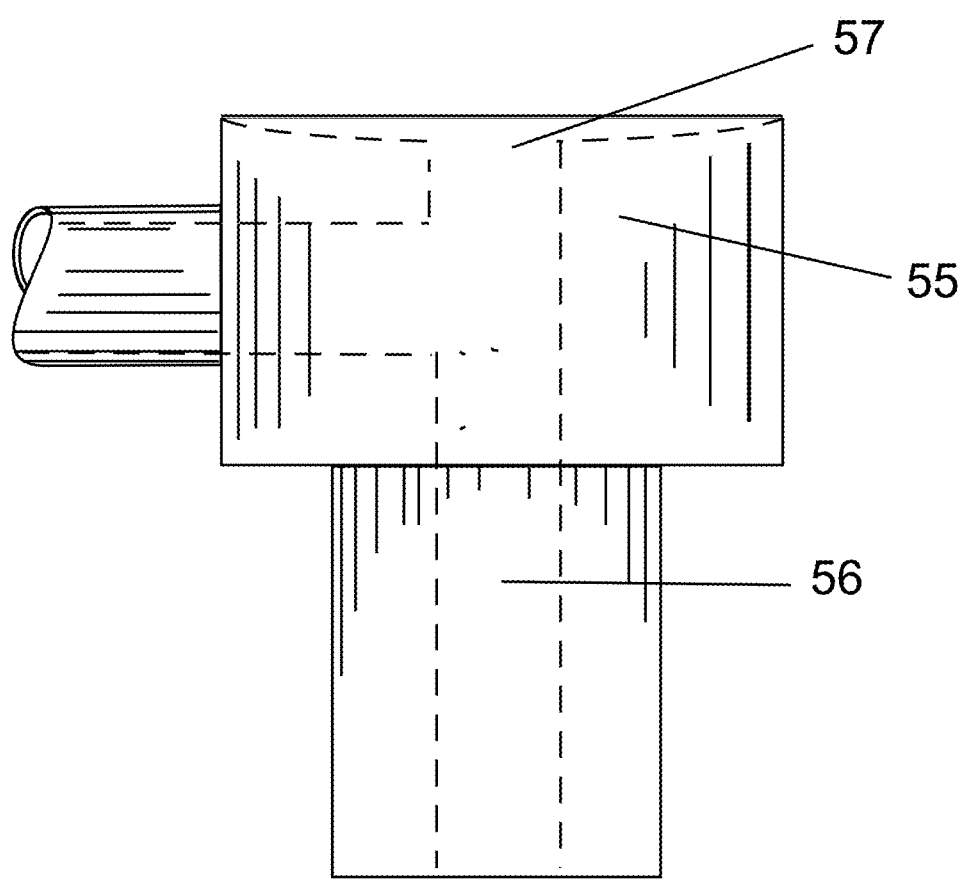
FIG. 8 is a view of one embodiment of a valve.

FIG. 8 shows detail of one embodiment of valve (55).

Figure 9A:
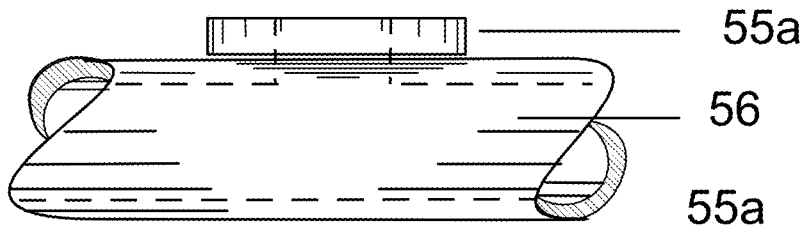
FIG. 9A is a left orthogonal view of FIG. 9.
Figure 9:
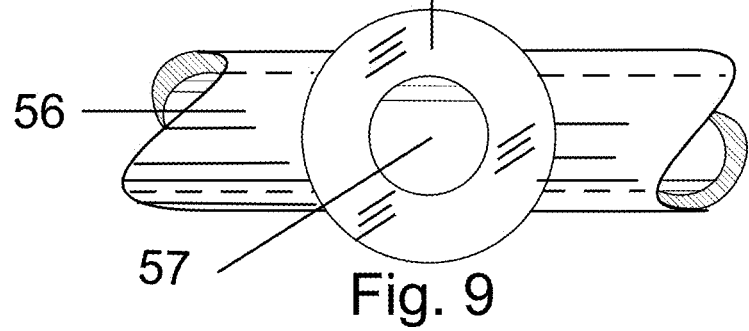
FIG. 9 is another embodiment of a valve

FIGS. 9 and 9A shows an alternative embodiment of valve (55A).

Figure 10A:
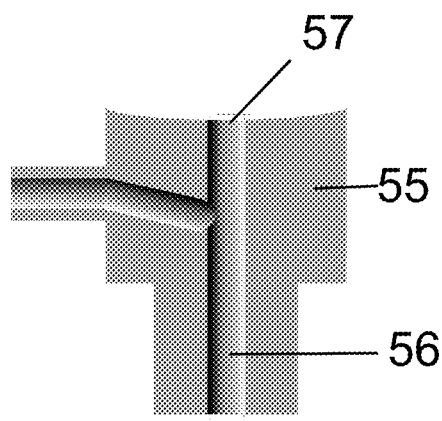
FIG. 10A is a solid cutaway view of FIG. 10.
Figure 10:
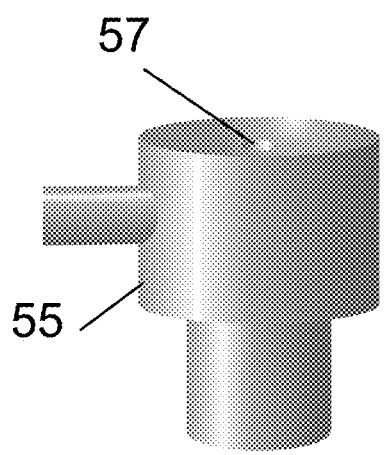
FIG. 10 is a solid perspective view of FIG. 5.

FIG. 10 shows a solid view of an embodiment of valve (55).

FIG. 10A shows s cross sectional view of FIG. 10.

Figure 11A:
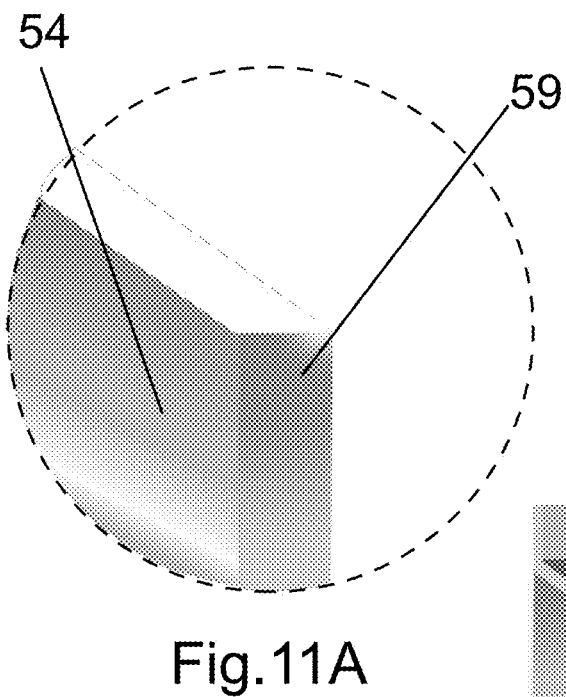
FIG. 11A is a close up view of area indicated in FIG. 11.
Figure 11:
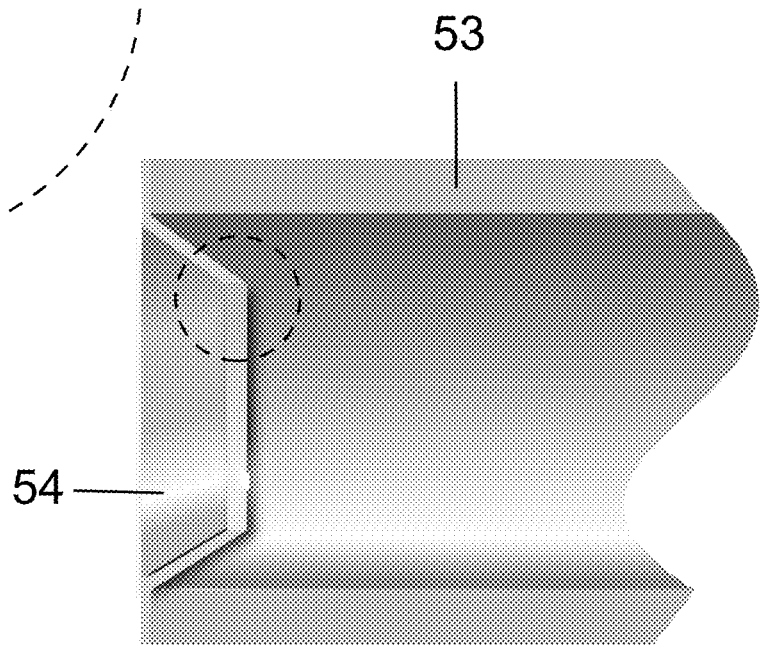
FIG. 11 is a solid orthogonal cutaway view of FIG. 7.

FIG. 11 Illustrates a solid cross sectional view of the construction details of distal end of the tube (53) and disposition of cutting element (54).

FIG. 11A Is a solid cross sectional close up detail of FIG. 11.

Figure 12:
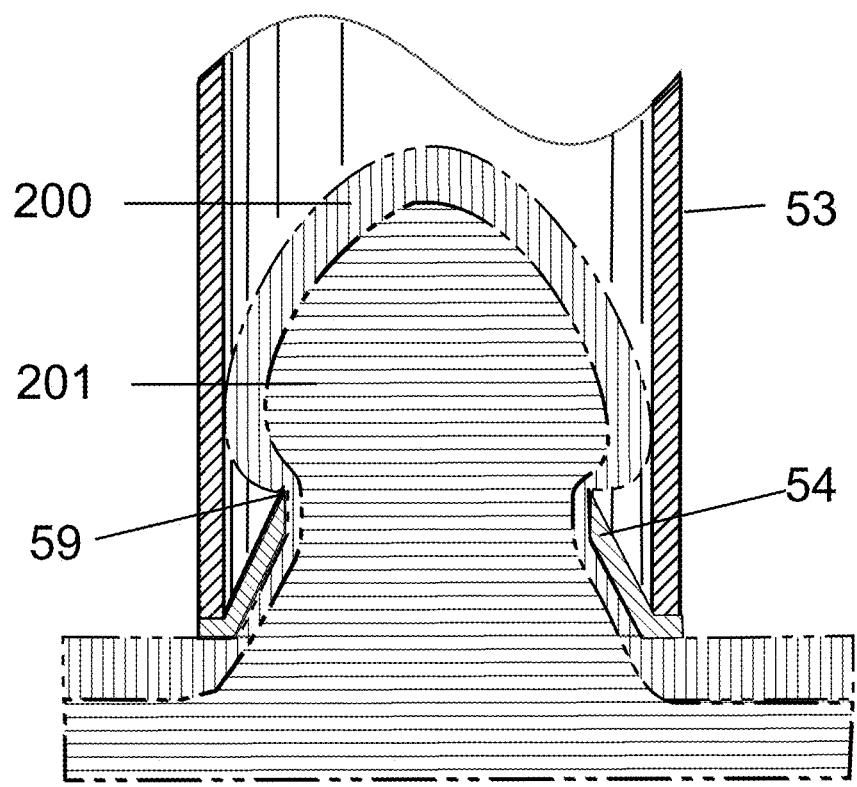
FIG. 12 is a cutaway view of how the element engages a specimen.

FIG. 12 is an illustration of the in which cutting edge (59) device is positioned to transect a sample of the mucosa (200).

FIG. 13 illustrates another embodiment of the device as it is to be used. Valve (55a) is attached to suction tubing (104) leading to a suction device (not shown).

Operation

The first embodiment of the device in FIG. 1 is introduced into the instrument channel (101) of an endoscope with the valve (55) disposed in place of the suction port (102). The catheter (51) is advanced until the distal end (53) contacts the intended biopsy site. The fenestration (57) is covered by a finger, transmitting suction to the lumen of the catheter (51), thereby drawing a tissue sample through cutting element (54). Withdrawal of the proximal end of the catheter (52) a short distance will cause cutting element (54) to transect the specimen. Suction will cause the specimen to be transported through the catheter (51) to a collection device. Repetition of this operation will allow the collection of a multitude of specimens without withdrawal of the device.

An alternative embodiment differs from the first in that valve (55a) does not replace suction port (102), but instead is attached to a separate suction and collection devices. Fenestration (57a) is covered by a finger, transmitting suction to the lumen of catheter (51)

The advantages of these embodiments are simplified construction, efficient specimen collection and shortened procedure time.

CONCLUSION

Endoscopic biopsy is an essential tool of medicine. It, however, entails costs and risk. This embodiment, through its simplicity, has the capability of reducing procedure time, anesthetic exposure, and manufacturing cost, while at the same time increasing reliability.

While the above description contains many specificities, these should not be construed as limitations on the scope, but rather an exemplification of one embodiment thereof. Other variations are possible. For example, other embodiments may be adapted to use on accessible tissues, independent of an endoscope, such as oral or gynecologic sites.

Accordingly, the scope should be determined not by the embodiment illustrated, but by the claims and their legal equivalents.

What is claimed is:

1. An endoscopic biopsy device for collecting multiple tissue samples from a body, comprising:
    an elongate tube comprising a distal end, a proximal end, and a lumen extending from the distal end to the proximal end;
    a cutting member disposed in an opening of the distal end of the elongate tube, the cutting member being immovable relative to the elongate tube, wherein the cutting member comprises:
        a hollow truncated cone having a truncated end comprising a cutting surface that maintains a fixed radial distance from the elongate tube and that faces into the elongate tube and away from the distal end of the elongate tube, wherein the cutting surface has a contiguous perimeter, and wherein the truncated end is angled relative to a longitudinal axis of the elongate tube such that the cutting member has a shape of a right circular hollow cone or an oblique oval hollow cone; and
        a blunting surface that faces outward from the elongate tube; and
    a valve disposed proximate to the proximal end of the elongate tube, wherein the valve is open to ambient air and attached to a suction device;
    wherein the endoscopic biopsy device is configured to collect the multiple tissue samples from the body and to transport the multiple tissue samples outside of the body without removal of the endoscopic biopsy device from the body.

2. The endoscopic biopsy device as recited in claim 1, wherein the elongate tube is of sufficient diameter, length, composition, and flexibility to be slidably disposed in an instrument channel of an endoscope and to extend from a distal end of the endoscope.

3. The endoscopic biopsy device as recited claim 1, wherein the truncated end of the cutting member comprises a beveled edge.

4. The endoscopic biopsy device as recited in claim 1, wherein the cutting member comprises a flange at a base thereof that comprises the blunting surface, wherein the flange is angled relative to the longitudinal axis of the elongate tube and has a circular or oval shape.

5. The endoscopic biopsy device as recited in claim 1, wherein the truncated end of the cutting member is disposed axially within the lumen at the distal end of the elongate tube.

6. The endoscopic biopsy device as recited in claim 1, further comprising:
    a flange attached to the distal end of the elongate tube.

7. The endoscopic biopsy device as recited in claim 1, the cutting member having been manufactured by stamping, milling, or depositing material capable of retaining a sharp edge for the cutting surface.

8. The endoscopic biopsy device as recited in claim 1, wherein the valve is interposed between the proximal end of the elongate tube and the suction device.

9. The endoscopic biopsy device as recited in claim 8, wherein the valve is constructed such that at least partially blocking an opening of the valve transmits suction to the lumen of the elongate tube.

10. The endoscopic biopsy device of claim 1, wherein:
    the elongate tube is configured to draw tissue of the body into the distal end of the elongate tube responsive to actuation of the valve; and
    the cutting member is configured to cut the tissue while the tissue is drawn into the distal end of the elongate tube to create a tissue sample of the multiple tissue samples.

11. A method of collecting a tissue sample from a body using an endoscopic biopsy device, the method comprising:
    inserting a distal end of an elongate tube of the endoscopic biopsy device into an instrument channel of an endoscope, wherein the endoscopic biopsy device comprises:
        the elongate tube comprising the distal end, a proximal end, and a lumen extending from the distal end to the proximal end;
        a cutting member disposed in an opening of the distal end of the elongate tube, the cutting member being immovable relative to the elongate tube, wherein the cutting member comprises a hollow truncated cone having a truncated end comprising a cutting surface that maintains a fixed radial distance from the elongate tube and that faces into the elongate tube and away from the distal end of the elongate tube, wherein the cutting surface has a contiguous perimeter, and wherein the truncated end is angled and has a circular or oval shape, and wherein the cutting member comprises a blunting surface that faces outward from the elongate tube; and
        a valve disposed proximate to the proximal end of the elongate tube, wherein the valve is open to ambient air and attached to a suction device;
    positioning the cutting member into contact with a sampling site of the body;
    actuating the valve, causing a specimen to be drawn into the distal end of the elongate tube and to come into contact with the cutting surface of the cutting member; and
    partially withdrawing the elongate tube from the endoscope, causing the cutting surface to cut the specimen away from the body to create the tissue sample.

12. The method of claim 11, further comprising:
    drawing the tissue sample through the lumen of the elongate tube to an external collection device interposed between the valve and the suction device.

13. The method of claim 12, further comprising performing the following without removing the endoscopic biopsy device from the body:
    positioning the cutting member into contact with a second sampling site of the body;
    actuating the valve, causing a second specimen to be drawn into the distal end of the elongate tube and to come into contact with the cutting surface of the cutting member; and
    partially withdrawing the elongate tube from the endoscope, causing the cutting surface to cut the second specimen away from the body to create a second tissue sample; and drawing the second tissue sample through the lumen of the elongate tube to the external collection device interposed between the valve and the suction device, wherein the tissue sample and the second tissue sample are removed from the body without removing the endoscopic biopsy device from the body.

14. The method of claim 11, further comprising:
slidably translating the elongate tube into the instrument channel until the distal end of the endoscopic biopsy device appears in a visual field of the endoscope.

15. The method of claim 11, wherein actuating the valve comprises at least partially blocking an opening of the valve.

16. The method of claim 15, wherein at least partially blocking the opening of the valve is performed by covering the opening of the valve with a finger.

17. The method of claim 11, wherein the cutting surface of the cutting member comprises a beveled edge.

18. The method of claim 11, wherein the truncated end of the cutting member is disposed axially within the lumen at the distal end of the elongate tube.

\* \* \* \* \*